United States Patent [19]

Harper

[11] Patent Number: 4,907,592
[45] Date of Patent: Mar. 13, 1990

[54] SELF-SEALING CONNECTOR FOR ELECTRICAL LEADS FOR USE IN WET ENVIRONMENTS

[75] Inventor: Clair Harper, Palm Coast, Fla.
[73] Assignee: Cardiac Control Systems, Inc., Palm Coast, Fla.
[21] Appl. No.: 282,504
[22] Filed: Dec. 12, 1988
[51] Int. Cl.$^4$ ............................................. A61N 1/00
[52] U.S. Cl. ................................................ 128/419 P
[58] Field of Search .......................... 128/419 P, 784; 439/810, 815

[56] References Cited

U.S. PATENT DOCUMENTS

| | | | |
|---|---|---|---|
| 4,180,078 | 12/1979 | Anderson | 128/419 P |
| 4,432,764 | 2/1984 | Lopez | 604/283 |
| 4,432,766 | 2/1984 | Bellotti et al. | 604/283 |
| 4,764,132 | 8/1988 | Stutz, Jr. | 439/810 |
| 4,784,141 | 11/1988 | Peers-Tavarton | 128/419 P |

Primary Examiner—Francis Jaworski
Assistant Examiner—George Manuel
Attorney, Agent, or Firm—Kerkam, Stowell, Kondracki & Clarke

[57] ABSTRACT

A connector for connecting catheters to a body implantable device utilizes an insulating, highly viscous material behind a punched through solid material through which a set screw wrench can be inserted. The viscous material provides insulation after removal of the set screw wrench.

4 Claims, 1 Drawing Sheet

SELF-SEALING CONNECTOR FOR ELECTRICAL LEADS FOR USE IN WET ENVIRONMENTS

FIELD OF THE INVENTION

This invention relates to a self-sealing connector for use with electrical pacemaker leads particularly sensors such as thermistors used for measuring blood temperature in rate-responsive pacemakers having high impedance which are effected by fluid intrusion in the connector assembly.

BRIEF DESCRIPTION OF THE INVENTION

A connector for an electrical lead of a body implantable device comprising a conductive block having electrical connection to a pacemaker sensor encased in a fluid impervious material, a first opening in the conductive block adapted to receive an electrical lead, a second threaded opening in the conductive block intersecting the first opening, a threaded set screw in said second opening, a resilient screw plug closing the outer end of the second opening, and a viscous fluid impervious material between the inner end of the screw plug and the outer end of the set screw.

DETAILED DESCRIPTION OF THE INVENTION

Figure 3:
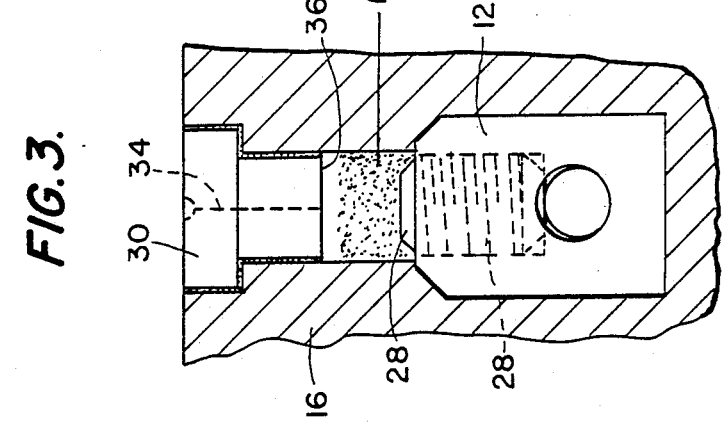
FIG. 3 is a enlarged end view of the connector.
Figure 1:
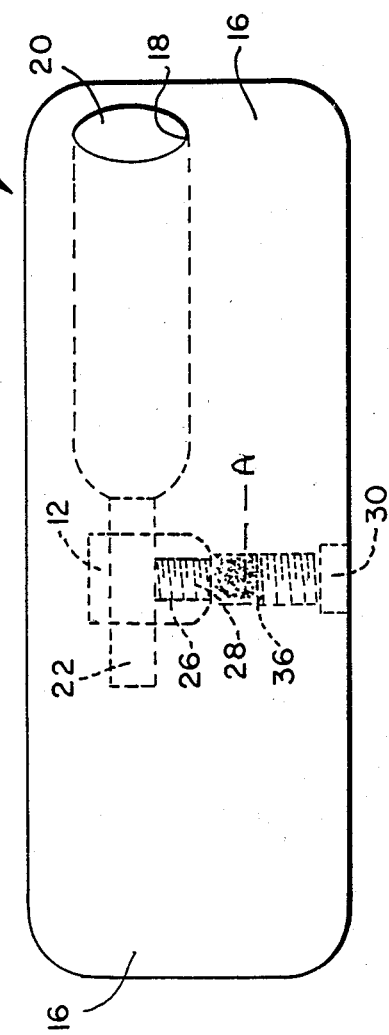
FIG. 1 is a top view of the connector of the invention.

Referring to the drawings, 10 generally designates the connector of the invention and elements related thereto.

Figure 2:
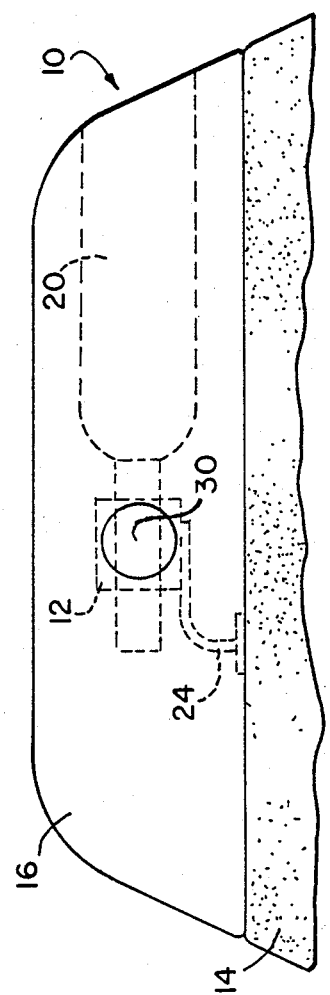
FIG. 2 is a front view of the structures shown in FIG. 1.

The connector 10 comprises a metallic body portion 12 preferably fabricated from a metal compatible with body fluids such as surgical steel. The connector block 12 is attached to a pacemaker or a pacemaker sensor 14. The assembly, the connector 12 and the body implantable device 14, are enclosed in an epoxy or silicone rubber coating 16 as better illustrated in FIG. 3. An opening 18 is made in the epoxy or silicone rubber enclosure at 18 to receive a lead 20 having a conductive tip 22. The block 12 has electric connection internally via conductor 24 best seen in FIG. 2 of the drawings.

The connector block is bored and tapped as at 26 to receive a set screw 28 which such screw holds the conductive end 22 of the lead 20 in the first bore in the connector block 12. The opening to the set screw extends outwardly through the silicone or epoxy covering and the remote end is closed by a silicone screw plug 30. The set screw is usually the type which is manipulated by a hex wrench. The wrench is inserted through the screw plug which is adhesively bonded to the housing and has a punch through indicated at 34, FIG. 3. This minimizes the fluid path size between the set screw and the body fluid environment.

To insure a body fluid tight seal between the inner end 36 of the silicone plug 30 and the outer end of the set screw 26 is maintained a viscous insulative material such as silicone grease or silicone gel A through which the set screw wrench is inserted. The grease or gel is displaced by the wrench during wrench insertion, but then reforms to block the direct conductive fluid path between the environment of the body and the connector block set screw assembly thereby achieving a fully fluid insulated connection.

What is claimed:

1. A connector system for an electrical lead of a body implantable device, comprising a connector block having an electrical connection to a sensor encased in a fluid-impervious material; a first opening in the connector block adapted to receive an electrical conductor; a second threaded opening in the connector block intersecting the first opening; a threaded set screw in said second opening; said set screw having an outer end and an inner end; a resilient screw plug closing the outer end of the second opening; said screw plug having an outer end of an inner end; and a viscous, fluid-impervious material between the outer end of the set screw and the inner end of the screw plug.

2. The connector system, as defined in claim 1, wherein the fluid-impervious material encasing the connector block comprises an epoxy or silicone rubber.

3. The connector system, as defined in claim 1, wherein the viscous, fluid-impervious material comprises a silicone gel or grease.

4. The connector system, as defined in claim 3, wherein the connector is encased in epoxy or silicone rubber.

* * * * *